United States Patent
Gandhi et al.

[11] Patent Number: 6,156,053
[45] Date of Patent: Dec. 5, 2000

[54] DUAL CATHETER ASSEMBLY

[75] Inventors: Deepak R. Gandhi; Cecily M. Hillsman, both of San Jose; Anant V. Hegde, Newark; Harm TenHoff, Mountain View, all of Calif.

[73] Assignee: Intella Interventional Systems, Inc., Sunnyvale, Calif.

[21] Appl. No.: 09/071,018

[22] Filed: May 1, 1998

[51] Int. Cl.$^7$ .................................................. A61M 29/00
[52] U.S. Cl. .......................................... 606/194; 604/101
[58] Field of Search ................... 604/101, 102, 604/96; 606/108, 194

[56] References Cited

U.S. PATENT DOCUMENTS

| | | | |
|---|---|---|---|
| 4,715,378 | 12/1987 | Pope, Jr. et al. | 128/344 |
| 4,744,366 | 5/1988 | Jang | 128/344 |
| 4,881,547 | 11/1989 | Danforth | 128/344 |
| 5,035,686 | 7/1991 | Crittenden et al. | 604/96 |
| 5,045,061 | 9/1991 | Seifert et al. | 604/101 |
| 5,102,390 | 4/1992 | Crittenden et al. | 604/101 |
| 5,141,494 | 8/1992 | Danforth et al. | 604/96 |
| 5,158,548 | 10/1992 | Lau et al. | 604/96 |
| 5,226,889 | 7/1993 | Sheiban | 604/101 |
| 5,338,301 | 8/1994 | Diaz | 604/96 |
| 5,364,347 | 11/1994 | Jang | 604/53 |
| 5,484,412 | 1/1996 | Pierpont | 604/101 |
| 5,501,668 | 3/1996 | Kontos | 604/96 |
| 5,505,699 | 4/1996 | Forman et al. | 604/96 |
| 5,725,535 | 3/1998 | Hegde et al. | 606/108 |
| 5,846,246 | 12/1998 | Dirks et al. | 606/108 |

FOREIGN PATENT DOCUMENTS

| | | | |
|---|---|---|---|
| 0213748 A1 | 3/1987 | European Pat. Off. | A61M 29/02 |
| 0380227 A2 | 8/1990 | European Pat. Off. | A61M 29/02 |
| 0747088 A1 | 12/1996 | European Pat. Off. | A61M 2/06 |
| WO 95/16487 | 6/1995 | WIPO | A61M 31/00 |
| WO 96/13297 | 5/1996 | WIPO | A61M 29/00 |

OTHER PUBLICATIONS

U.S. application No. 08/876,999, Imran et al., filed Jun. 16, 1997.

U.S. application No. 08/949,726, Hegde et al., filed Oct. 14, 1997.

*Primary Examiner*—Michael Buiz
*Assistant Examiner*—Kevin Truong
*Attorney, Agent, or Firm*—Limbach & Limbach LLP

[57] ABSTRACT

The present invention relates to a combination device comprising two catheters, or a dual catheter assembly, for use in vascular procedures wherein the shaft of the first catheter functions as a guidewire for the second catheter. The dual catheter assembly comprises a first balloon catheter and a second balloon catheter wherein the second balloon catheter is slidably disposed on the shaft of the first balloon. In preferred embodiments, the first catheter is a low profile balloon on a wire catheter and the second catheter is a full size balloon catheter having a plurality of balloons mounted thereon. Optionally, a stent is carried by at least one of the balloons on the second catheter. In more preferred embodiments, the second catheter includes a manifold that may be used to inflate and deflate any combination of the plurality of balloons via a single port. The dual catheter assembly of the present invention is especially useful in vascular procedures such as angioplasty, progressive/multiple angioplasty, and stent delivery.

33 Claims, 8 Drawing Sheets

DUAL CATHETER ASSEMBLY

BACKGROUND

The present invention generally relates to medical catheters. More particularly, the present invention relates to a combination device comprising two catheters, or a dual catheter assembly, for use in vascular procedures wherein the shaft of the first catheter functions as a guidewire for the second catheter.

Although used in a variety of medical procedures, multiple balloon catheters are most widely associated with percutaneous transluminal coronary angioplasty. The procedure typically involves advancing a balloon catheter to the partially blocked coronary artery and inflating one or more balloons at the blockage site. The inflated balloons stretch and/or fracture the blockage thereby enlarging the opening of the occluded vessel. In some cases, a stent is also deployed to further enlarge the opening and to prevent the weakened vessel from collapsing.

In general, separate balloon catheters are used for performing angioplasty and for delivering stents. As a result, a physician performing angioplasty followed by stent implantation may use multiple devices. For example, the procedure may start with a floppy tip guidewire followed by a low profile balloon catheter riding over the guidewire to predilate an occluded vessel. Once the vessel is predilated, progressively larger balloon catheters may be navigated to the stenosis, used and then withdrawn in succession to sufficiently enlarge the opening. Finally, another balloon catheter bearing a stent may be used to deliver the stent to the lesion site.

Attempts have been made to design devices that perform more than one function during vascular procedures. For example, U.S. Pat. No. 5,035,686 discloses a low profile balloon on a wire catheter that is designed to also act as guidewire for a second catheter. Because the low profile balloon catheter may also function as an independent guidewire, it would remain in the vessel and any subsequent catheter would be threaded over its shaft. However, because the subsequent devices are necessarily off-the-shelf catheters often made by different manufacturers, the desired combination of catheters either may not work well together, or may not be compatible with each other.

Another example of a catheter that performs more than one function is described by U.S. Pat. No. 5,226,889 which discloses a multiple balloon catheter wherein one of the balloons carries a stent. The idea behind this device is that this single catheter may be used for performing both angioplasty and stent delivery. However, multiple catheters are still required in most cases. Due to the stent, these combination catheters typically have larger profiles and thus are not generally able to navigate the occluded vessel without the vessel being pre-dilated. Depending on the nature and extent of the occlusion, more than one successively larger balloon catheter may be required to sufficiently open the blockage so that it may accommodate the larger profile of the combination catheter.

In summary, a product that is designed to be used for all aspects of angioplasty and stent delivery would be desirable. Because predilation and stent delivery may be performed with a single product, the use of such a device would maximize efficiency and minimize catheter exchange.

SUMMARY OF THE INVENTION

The present invention relates to a single product for performing multiple vascular procedures. Comprising two catheters, or a dual catheter assembly, the combination device is particularly suited for use in angioplasty and stent delivery.

The dual catheter assembly comprises a first balloon catheter and a second balloon catheter wherein the second catheter is slidably disposed on the shaft of the first catheter. In preferred embodiments, the first catheter is a low profile balloon on a wire catheter and the second catheter has a plurality of balloons mounted thereon. Optionally, a stent is carried by at least one of the balloons on the second catheter. In more preferred embodiments, the second catheter includes a manifold that may be used to inflate and deflate any combination of the plurality of balloons via a single port. Because the two catheters are especially designed to work together, the dual catheter assembly efficiently and seamlessly performs all aspects of both angioplasty and stent delivery procedures.

DESCRIPTION OF THE PREFERRED EMBODIMENTS

The present invention relates to a dual catheter assembly, or a combination device that is particularly well suited for all aspects of both angioplasty and stent delivery procedures. In the most general terms, the dual catheter assembly comprises a first balloon catheter and a second balloon catheter wherein the second catheter is slidably disposed on the shaft of the first catheter. Although not required for the practice of the present invention, it is preferred that the first catheter is a low profile balloon on a wire catheter, and the second catheter is a multiple balloon catheter which has at least one balloon that is larger than that mounted on the first catheter. Although either catheter may optionally carry a stent, it is generally preferred that the stent be carried by at least one of the balloons on the second catheter. In more preferred embodiments, the second catheter includes a manifold that may be used to inflate and deflate any combination of the plurality of balloons via a single port.

Figure 1:
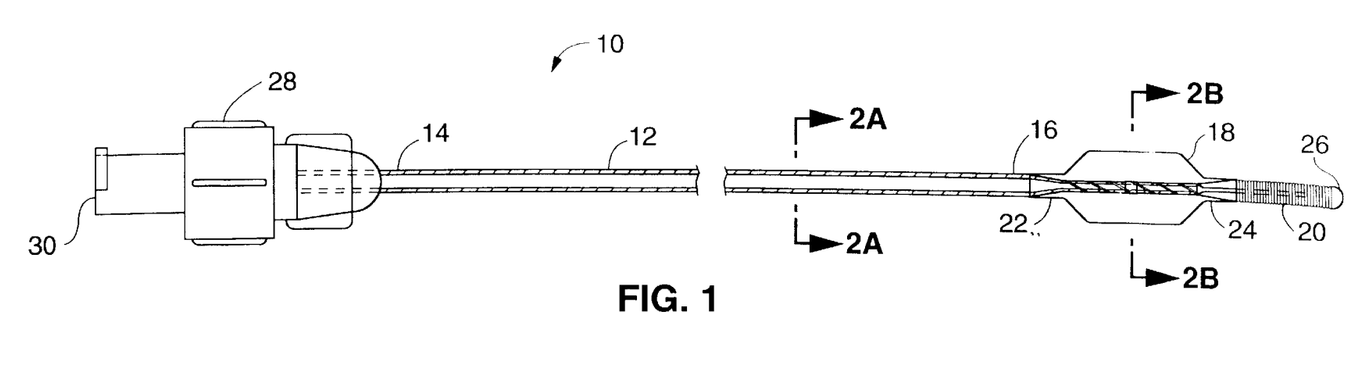
FIG. 1 is a side view of one embodiment of the first catheter of the dual catheter assembly.

FIG. 1 illustrates a preferred embodiment of a first catheter 10 which together with a second catheter forms the dual catheter assembly. First catheter 10 may be of any size (i.e. diameter and length) that may be useful in coronary procedures and comprises an elongated shaft 12 having a proximal end 14 and a distal end 16.

Although not necessary to the practice of the present invention, it is generally preferred that first catheter 10 is a low profile catheter whose shaft 12 has a sufficiently small outside diameter such that a second catheter may be slidably disposed over shaft 12, and both catheters may be inserted into a coronary vessel. Typically, the outside diameter of shaft 12 is between about 0.005 and about 0.035 inches, more preferably between about 0.01 and about 0.015 inches, and a double wall thickness is between about 0.001 and about 0.015 inches, more preferably between about 0.001 and about 0.003 inches. However, values for both the outside diameter and double wall thickness may be outside of these ranges.

Shaft 12 may be formed of any suitable material known in the art that is both sufficiently rigid and flexible to navigate the coronary passageways. Optionally, to prevent unnecessary vessel trauma, approximately about 15 to about 50 centimeters of the distal end 16 of shaft 12 can be more flexible than the remaining portion of shaft 12 so that catheter 10 may more easily yield when advanced against obstacles. This may be achieved by either using a different more flexible material or using a different processing method (while using the same material) than that used to form the remaining portion of shaft 12. Illustrative examples of suitable shaft materials include metals such as stainless steel and shape memory alloys such as various nickel titanium blends (which are also known in the art as Nitinol). The outside surface of shaft 12 may optionally be coated with polymeric materials to provide a more lubricious surface to facilitate the navigation of catheter 10 through the coronary vessels.

The distal portion 16 of shaft 12 includes at least one balloon 18 mounted thereon and floppy tip 20. Because the first catheter also functions as a guide wire for the second catheter, the first catheter is sometimes referred to as a balloon on a wire catheter. Balloon 18 may be formed of any suitable material known in the art. Illustrative examples include non-compliant materials such as polyethylene terephthalate and semi-compliant materials such as various homopolymers and copolymers of Nylon. Additives like plasticizers and stabilizers for manipulating balloon characteristics such as strength and processability may also be included.

The proximal and distal ends 22 and 24 of balloon 18 are bonded to shaft 12 using conventional methods like adhesives or thermal bonding (also known as heat sealing) to form a fluid tight seal. Because catheter 10 is typically a low profile catheter, balloon 18 mounted thereon typically will be smaller than those found on conventional catheters. In preferred embodiments, balloon 18 has a length between about 12 and about 30 millimeters, a double wall thickness between about 0.001 and about 0.003 inches, and an inflated diameter of between about 1.0 and about 4.0 millimeters, more preferably between about 1.5 and about 3.0 millimeters. In preferred embodiments, balloon 18 is capable of withstanding pressures of at least about 8 atmospheres and more preferably withstanding pressures between about 14 to about 20 atmospheres.

If more than one balloon is mounted on catheter 10, it is preferred that the plurality of balloons are placed in tandem (one right behind another) after the most distal balloon 18 along the distal portion 16 of shaft 12. In more preferred embodiments, each balloon added after the most distal balloon 18 is successively larger than the previously placed balloon. The tandem arrangement, in contrast to the concentric balloon arrangement, makes it more likely that catheter 10 will maintain its generally smaller profile.

Floppy tip 20 is preferably attached at the most distal end 16 of shaft 12 using conventional means such as adhesives, thermal bonding, welding, soldering, and brazing, and is preferably formed of a suitable radiopaque material such as gold or a platinum tungsten alloy. A solder bead or weld 26 is attached to the distal end of floppy tip 20 to provide an atraumatic, hemispherical frontal surface.

As its name implies, floppy tip 20 is preferably more flexible than distal end 16 of shaft 12, and may be of any suitable length. However, lengths between about 2 and about 8 centimeters are preferred and lengths between about 3 and about 5 centimeters are even more preferred. To maximize flexibility, floppy tip 20 in a form of a coil as shown by FIG. 1 is generally preferred. Optionally, floppy tip 20 may be manufactured with a slight bend (i.e. preshaped in a shape of a "J") to aid in steering catheter 10. Alternatively, floppy tip 20 may be shaped into a desired bend by the catheter operator immediately before use.

Attached to the most proximal end 14 of shaft 12 is fitting 28 which makes a fluid tight seal and includes at least one port 30 which is in communication with one or more lumens within shaft 12. Illustrative examples of fitting 28 are a Touhy-Borst adapter which with a threaded cap which engages a sealing member and a Touhy-Borst adapter with a Luer lock. Fitting 28 may also be used as a means for applying torque and may optionally be removable from shaft 12. For example, it may be desirable to remove fitting 28 to further extend the length of shaft 12 by conventionally attaching a guidewire extension thereon.

Figure 2A:
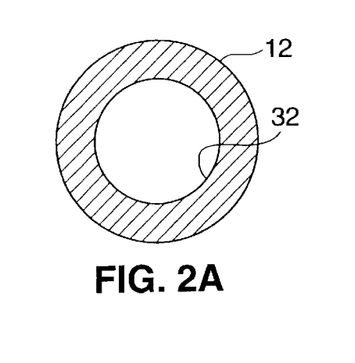
FIG. 2A is a cross section at position A—A of the first catheter illustrated by FIG. 1.
Figure 2B:
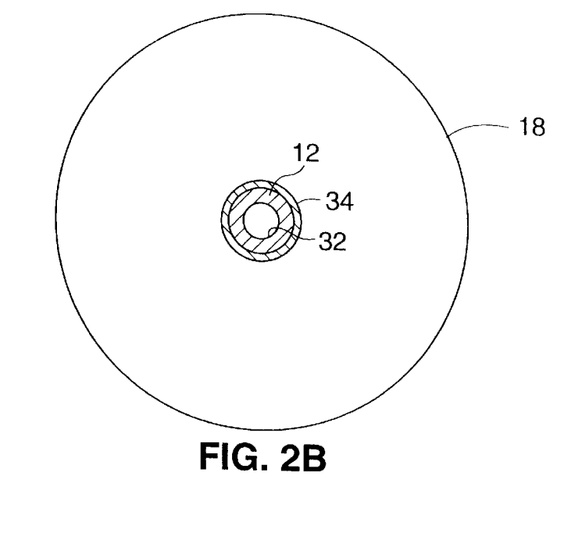
FIG. 2B is a cross section at position B—B of the first catheter illustrated by FIG. 1.

FIG. 2A is a cross-section of catheter 10 at position A—A which shows lumen 32 within shaft 12. FIG. 2B is a cross-section of catheter 10 at position B—B which shows balloon 18 surrounding shaft 12. A radiopaque marker band 34 made from conventional materials is preferably disposed between proximal and distal ends 22 and 24 of balloon 18 so that the location of balloon 18 may be visualized while catheter 10 is being used.

Figure 3:
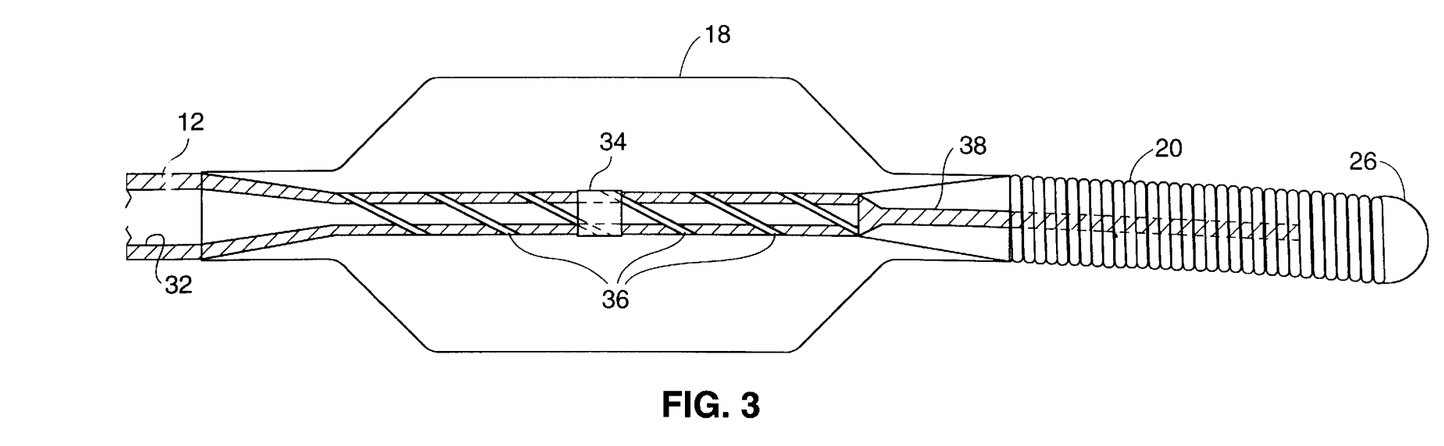
FIG. 3 is an enlarged view of the distal end of the first catheter illustrated by FIG. 1.

FIG. 3 is an enlarged view of the distal end of catheter 10. As illustrated by FIG. 3, the portion of shaft 12 that is surrounded by balloon 18 may be optionally tapered to a smaller diameter than the remaining sections of shaft 12. In addition, one or more slots 36 are formed in shaft 12 to provide access from the inflation/deflation port 30 through lumen 32 to balloon 18. In preferred embodiments, shaft 12 contains a plurality of slots 36 so that balloon 18 may be rapidly inflated and deflated. In addition to providing access to balloon 18, slots 36 also provide additional flexibility to distal end 16 of catheter 10.

Slots 36 may be of any suitable size. Illustrative examples include rectangular slots being spaced apart a distance of between about 1 and 4 millimeters, more preferably between about 2 and about 3 millimeters and having dimensions between about 0.5 and about 1 millimeters by between about 0.1 and about 0.5 millimeters. However, the length and width of the slots as well as their spacings may be outside of these ranges. Alternatively, slots 36 may be a single lead helical path.

Catheter 10 may optionally include a core wire. This core wire may extend the entire length of catheter 10 such that it extends through shaft 12 and floppy tip 20 (terminating into weld 26), or may extend only a portion of catheter 10. In preferred embodiments, core wire 38 is provided only at the distal end of catheter 10. As illustrated by FIG. 3, core wire 38 is attached to shaft 12 using conventional means such as adhesives and thermal bonding, and extends into a portion of floppy tip 20.

Figure 4:
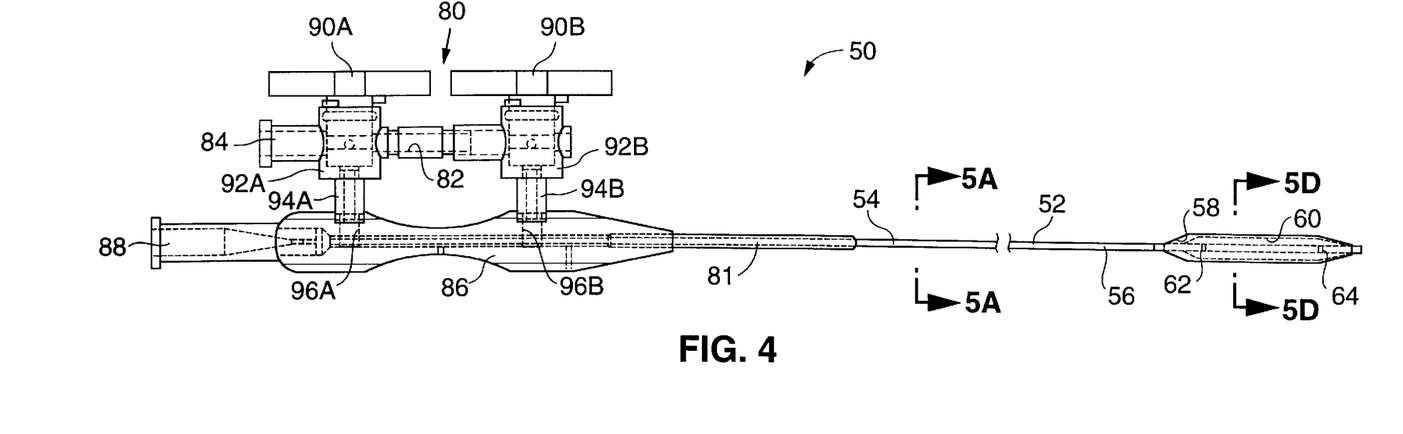
FIG. 4 is a side view of one embodiment of the second catheter of the dual catheter assembly.

FIG. 4 illustrates a preferred embodiment of a second catheter 50 which together with the just described first catheter, forms the dual catheter assembly of the present invention. Although the second catheter depicted in FIG. 4 is an over the wire ("OTW") catheter in which a guidewire is threaded through its entire length, the second catheter may also be a single operator exchange catheter ("SOE") in which a guidewire is threaded through only a portion of its distal length.

Second catheter 50 may be of any size (i.e. diameter and length) that may be useful in coronary procedures and comprises an elongated tubular member 52 having a proximal end 54 and a distal end 56, and one or more balloons mounted thereon. Elongate tubular member 52 may be formed of any suitable material such as various thermoplastic polymers (ie. polystyrene and polyethylene) and polyamides (i.e. Nylons). In preferred embodiments, the outside diameter of elongate tubular member is between about 0.025 and about 0.095 inches. An outside diameter of between about 0.035 and about 0.050 inches is especially preferred. The outside surface of elongate tubular member 52 may optionally be coated with polymeric materials to provide a more lubricious surface to facilitate the navigation of catheter 50 through the coronary vessels.

Although second catheter 50 may have any number of balloons, a plurality of balloons is generally preferred and may be formed from the same materials as previously described for the balloons mounted onto the first catheter. The plurality of balloons on second catheter 50 may be mounted on to elongated tubular member 52 in any arrangement. For example, the balloons may be in tandem, concentric, or a combination of both. In especially preferred embodiments and as depicted by FIG. 4, catheter 50 includes at least two concentric balloons, 58 (outer balloon) and 60 (inner balloon) and carries a stent thereon.

In preferred embodiments, balloon 58 has a length between about 12 and about 45 millimeters and more preferably is between about 18 and about 30 millimeters, double wall thicknesses between about 0.001 and about 0.015 inches, more preferably between about 0.001 and 0.003 inches, and has an inflation diameter between about 1.5 and about 12 millimeters. Because balloon 60 is placed within balloon 58, balloon 60 is necessarily smaller by between about 0.25 and about 2.0 millimeters, and has a length between about 11.5 and about 44.5 millimeters, and more preferably between about 17.5 and 29.5 millimeters, a double wall thicknesses between about 0.001 and about 0.015 inches, more preferably between about 0.001 and about 0.003 inches, and an inflation diameter between about 1 and about 12 millimeters. In preferred embodiments, balloons 58 and 60 are capable of withstanding pressures of at least about 8 atmospheres and more preferably between about 14 to about 20 atmospheres.

Both balloons 58 and 60 are bonded to elongate tubular member 52 at the respective balloon's proximal and distal ends using conventional methods like adhesives or thermal bonding to form a fluid tight seal. One or more conventional radiopaque markers 62 and 64 are placed at the appropriate places along elongate tubular member 52 to help identify the position of balloons 58 and 60 during use. Optionally, one of the balloons on second catheter 50 may also carry a stent (not pictured by FIG. 4).

Figure 5A:
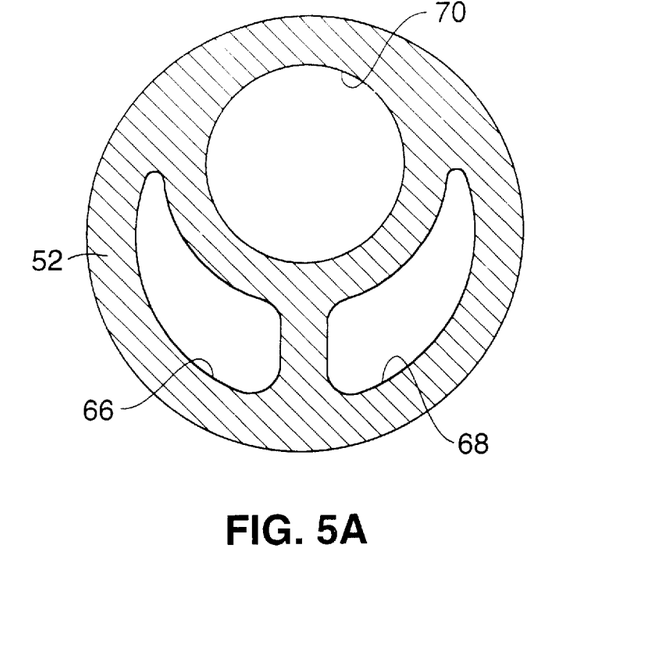
FIG. 5A is a cross section at position A—A of the second catheter illustrated by FIG. 4.

Communication to the one or more balloons are provided via multiple lumens formed within elongate tubular member 52. In preferred embodiments, a separate lumen is provided for each balloon mounted onto second catheter 50. FIG. 5A is a cross-section at position A—A of FIG. 4 and shows three lumens, one for each of the two balloons (lumens 66 and 68), and a third for the guidewire (lumen 70).

Because the catheter depicted by FIG. 4 is an over the wire catheter, lumen 70 extends through the entire length of elongated tubular member 52. If second catheter 50 were a single operator exchange catheter, an exit port would exist approximately between about 20 and about 40 centimeters, more preferably about 30 centimeters from the distal end of elongate tubular member 52.

Figure 5B:
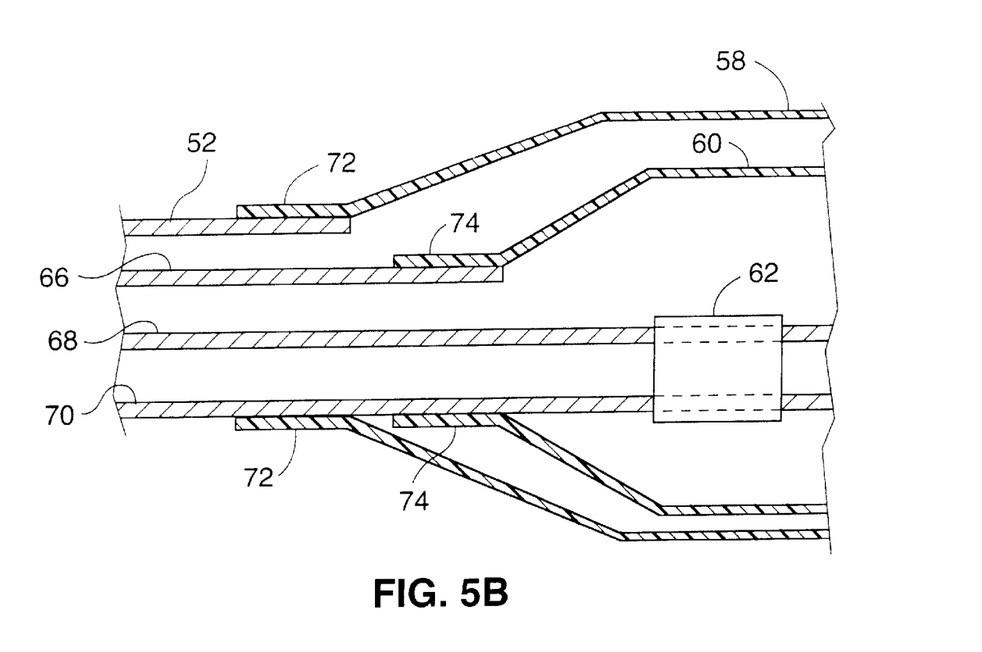
FIG. 5B is an enlarged side section of the second catheter illustrated by FIG. 4 at a position where the proximal ends of the concentric balloons are mounted onto the catheter shaft.
Figure 5C:
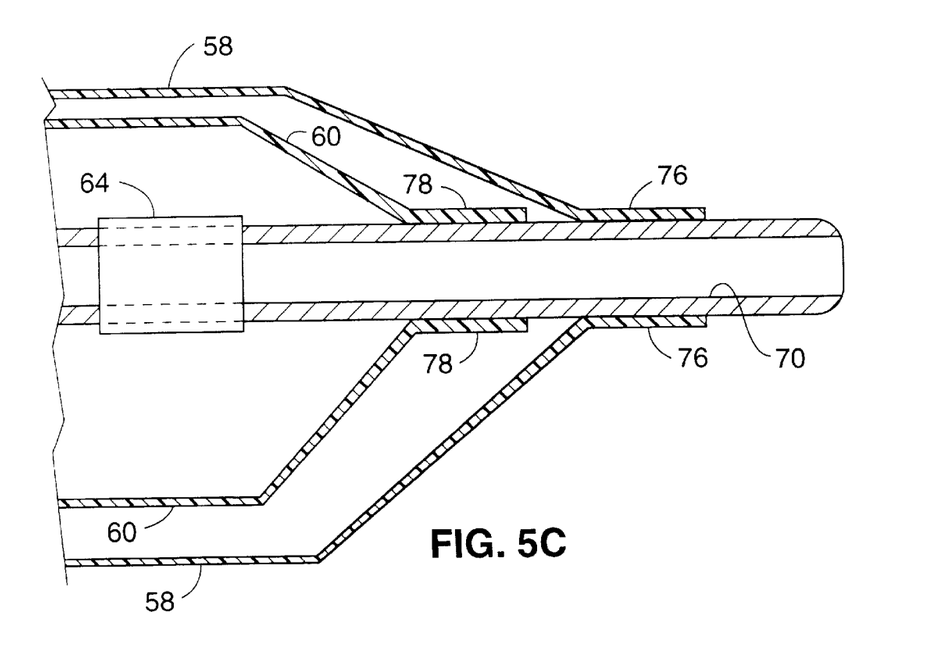
FIG. 5C is an enlarged side section of the second catheter illustrated by FIG. 4 at a position where the distal ends of the concentric balloons are mounted onto the catheter shaft.
Figure 5D:
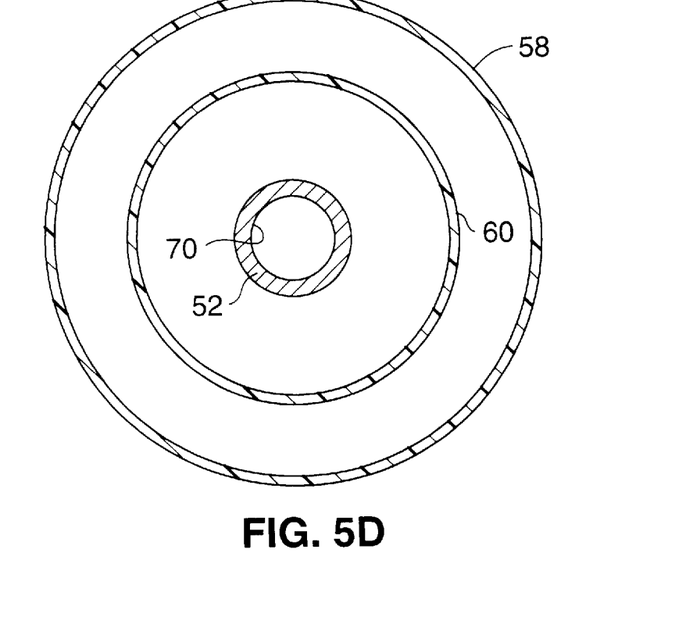
FIG. 5D is a cross section at position D—D of the second catheter illustrated by FIG. 4.

FIGS. 5B and 5C are enlarged side sectional views of the proximal and distal ends of balloons 58 and 60. As shown by FIG. 5B, lumens 66 and 68 terminate near their respective balloon's proximal adhesion points 72 and 74 at which point the lumens essentially become coextensive with the interiors of balloon 58 and balloon 60 respectively. Because only guidewire lumen 70 still needs to be accommodated beyond adhesion points 72 and 74, the diameter of the remaining portion of elongate tubular member 52 may be smaller than it was previously. FIG. 5C illustrates such a scenario whereby the diameter of elongate tubular member 52 is only sufficient to accommodate guidewire lumen 70 at the distal adhesion points 76 and 78 of balloons 58 and 60. This is also shown by FIG. 5D which is a cross-section at position D—D of FIG. 4 and shows that the only remaining lumen within elongate tubular member 52 after proximal adhesion points 72 and 74 is guidewire lumen 70.

Referring back to FIG. 4, proximal end 54 of elongate tubular member 52 is attached to manifold 80. Optionally, elongate tubular member 52 may include strain relief 81 along its portion which spans the vicinity immediately both inside and outside of manifold 80. Although any suitable manifold may be used with the dual catheter assembly, a manifold that allows any combination of the plurality of balloons to be independently inflated and/or deflated is generally preferred. This type of manifold is disclosed by U.S. Ser. No. 09/014,532 filed Jan. 28, 1998 entitled "MULTIPLE VALVE SINGLE PORT MANIFOLD" by inventors Thomas Michael Bourne, Anant Hegde, and Harm TenHoff which is incorporated herein by reference.

Manifold 80 comprises (i) conduit 82 having entry port 84; (ii) shaft 86 for containing elongated tubular member 52 therein, shaft 86 optionally having guidewire entry port 88 (for when second catheter 52 is an over the wire catheter); and, (iii) a plurality of valve gates 90 disposed within conduit 82 having an opened and a closed position.

Conduit 82 includes entry port 84 and a plurality of valve housings 92 for each valve gate 90, and is fluidly coupled to shaft 86 by connectors 94. Shaft 86 in turn includes a plurality of base channels 96 for continuing the connection to the balloon inflation/deflation lumens of elongate tubular member 52. At each junction where elongate tubular member 52 and base channel 96 meet within shaft 86, elongate tubular member 52 includes an opening to the corresponding balloon inflation/deflation lumen (lumens 66 or 68 which are not depicted by FIG. 4). As a result, when valve gates 90 are in an opened position, entry port 84 is fluidly coupled to balloon inflation lumens 66 and 68 via conduit 82 through connectors 94 and base channels 96.

Figure 5E:
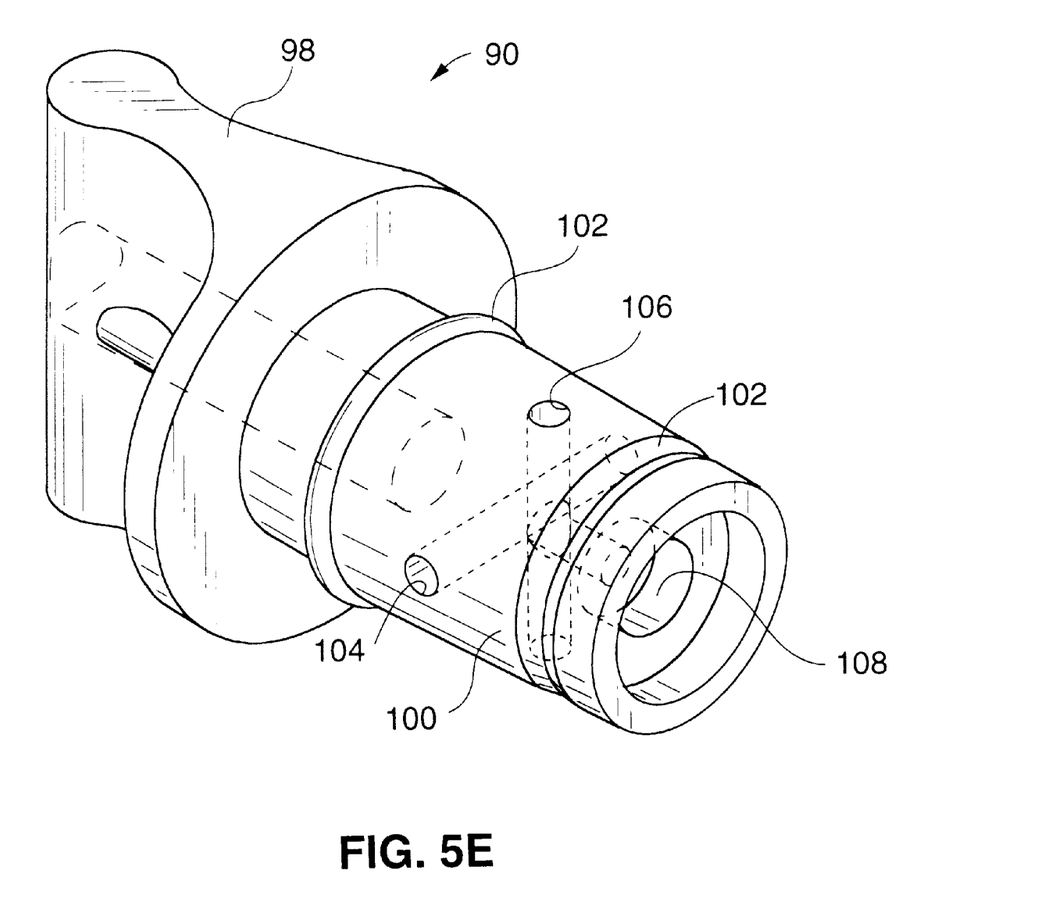
FIG. 5E is an enlarged schematic of a valve gate that is used in the manifold illustrated by FIG. 4.

Independent access to each balloon inflation lumen from a single entry port 84 is possible by a unique design for valve gate 90. As shown by FIG. 5E, valve gate 90 comprises handle 98 and stem 100. Stem 100 in turn includes seals 102 at its upper and lower portions, upper horizontal channel 104, lower horizontal channel 106, and vertical channel 108. Upper horizontal channel 104 and lower horizontal channel 106 are in different horizontal planes and are placed at an angle, preferably 90°, with respect to each other. However, an essential feature of the valve gate design is the placement of the upper horizontal channel 104 and lower horizontal channel 106 along stem 100 such that both are capable of being in fluid communication with conduit 82. Lower horizontal channel 106 is fluidly coupled to vertical channel 108, preferably connecting at 90° with respect to each other to form a T-shaped passageway.

Figure 5F:
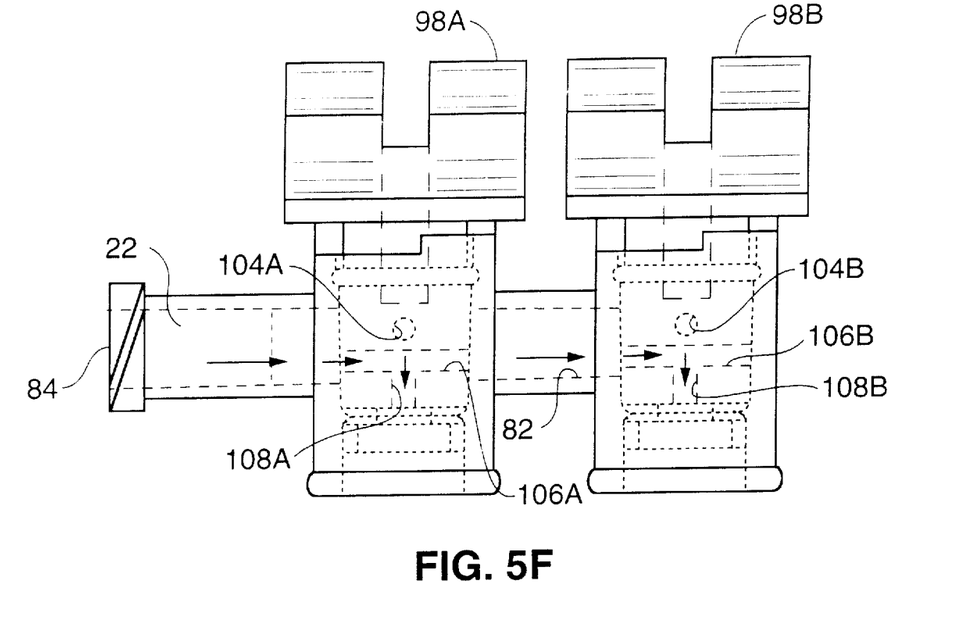
FIG. 5F is a side view of the manifold illustrated by FIG. 4 wherein both valve gates are in the opened position.

Operation of the valve gate will be further discussed with reference to FIGS. 5F and 5G. As shown by FIG. 5F, because the proximal valve gate 98A with respect to entry port 84 is in an opened position, entry port 84 is fluidly coupled to its corresponding balloon inflation lumen via lower horizontal channel 106A and vertical channel 108A. Proximal lower horizontal channel 106A also acts as a pass through channel to the distal valve gate 98B. Distal valve gate 98B, also being in an opened position is fluidly coupled to its corresponding balloon inflation lumen in a similar manner. The arrows indicate the direction of fluid flow.

Figure 5G:
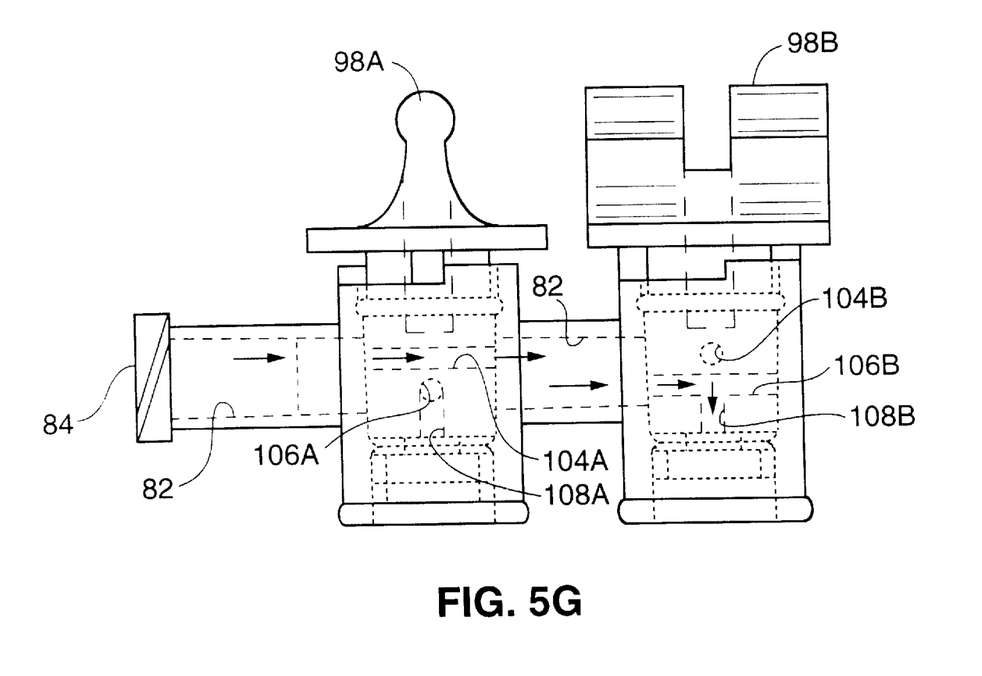
FIG. 5G is a side view of the same manifold as in FIG. 5F wherein one of the valve gates is in the closed position.

When proximal valve gate 98A is in a closed position (as depicted by FIG. 5G), upper horizontal channel 104A is fluidly coupled to entry port 84. Because upper horizontal channel is not coupled to vertical channel 108A, it can only act as a pass through channel to the distal valve gate 98B. As shown by FIG. 5G, lower horizontal channel 106B is fluidly coupled to vertical channel 108B which in turn allows access to the corresponding balloon inflation lumen. The combination of upper horizontal channel 104 and lower horizontal channel 106 allows each valve gate to control access to its corresponding catheter lumen without regard to the positions of the other valve gates.

Manifold 80 may be made of any suitable material known in the art. In preferred embodiments, rigid materials, such as polycarbonate and styrene, that are not easily compressible are preferred for forming the conduit 82, valve housings 92, shaft 86, connectors 94 and base channels 96. However, since some compressibility is desired for forming a tight seal between valve gates 90 and valve housings 92, slightly less rigid materials, such as polyethylene and polypropylene, are preferred for making the valve gates 90.

Figure 6A:
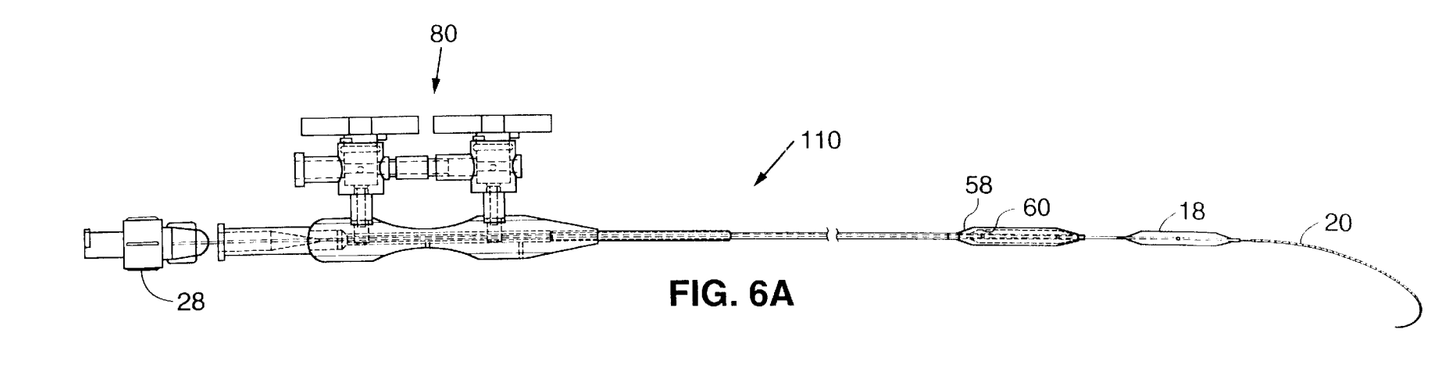
FIG. 6A is a side view of one embodiment of the dual catheter assembly wherein the second catheter is an over the wire catheter.
Figure 6B:
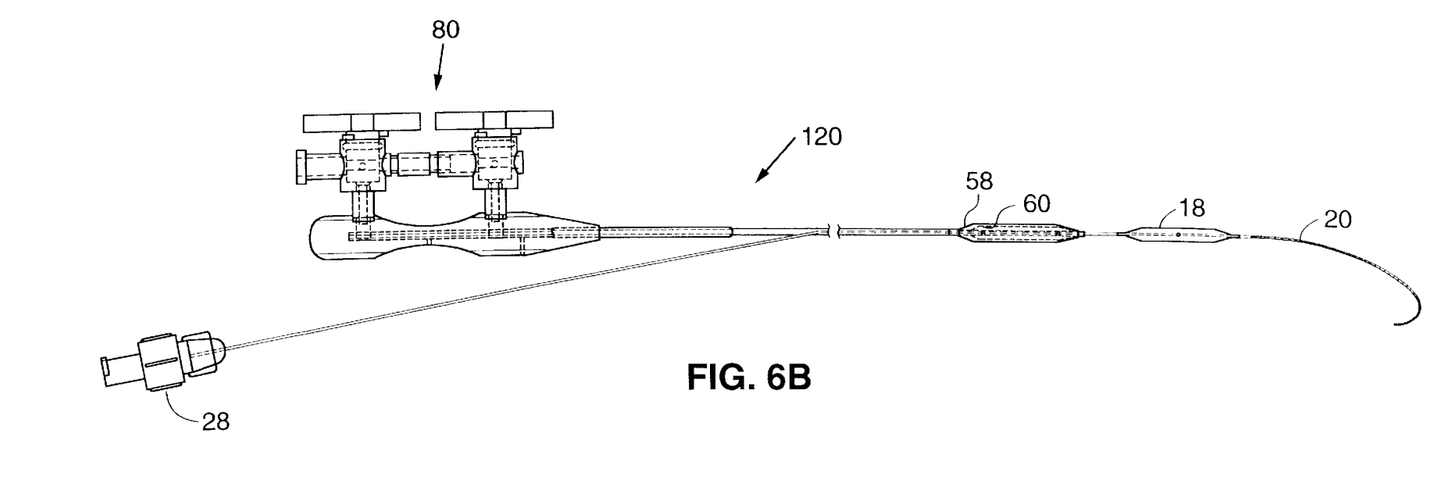
FIG. 6B is a side view of a second embodiment of the dual catheter assembly wherein the second catheter is a single operator exchange catheter.
Figure 6C:
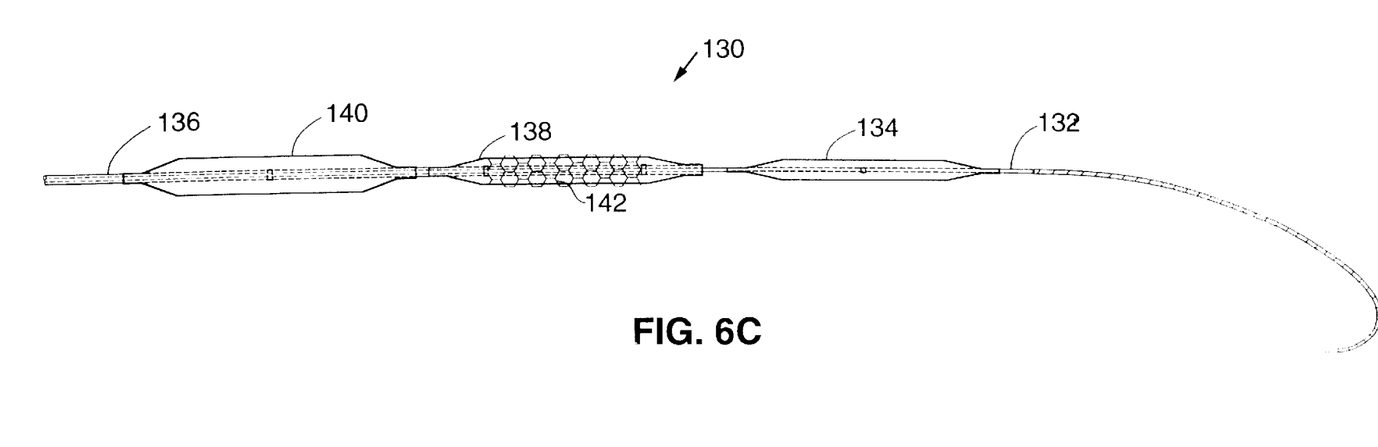
FIG. 6C is an enlarged view of the distal end of a third embodiment of dual catheter assembly wherein the second catheter includes two balloons in tandem wherein the most distal balloon of the second catheter also carries a stent thereon.

FIGS. 6A and 6B illustrates two embodiments of the dual catheter assembly of the present invention. Both first and second catheters in both Figures are generally similar to those previously described. However, FIG. 6A shows a dual catheter assembly 110 wherein the second catheter is a balloon on the wire catheter and FIG. 6B shows a dual catheter assembly 120 wherein the second catheter is a single operator exchange catheter. Similarly, FIG. 6C illustrates the distal end of a third embodiment 130 of the present invention. In this embodiment, the first catheter 132 is as previously described wherein it is a low profile single balloon on a wire catheter. However, second catheter 136 is a dual balloon catheter wherein balloons 138 and 140 are in a tandem arrangement. The most distal balloon or balloon 138 also carries stent 142 thereon.

Operation of the dual catheter assembly of the present invention will be illustrated with reference to the specific embodiment depicted by FIG. 6A. The combination device may be packaged pre-assembled (wherein the second catheter is slidably disposed over the first catheter) or may be assembled from the component pieces by a technician or physician immediately prior to the angioplasty procedure. If desired, a stent may be mounted onto an appropriate balloon, preferably on second catheter 50, by crimping it by hand or by a crimping device. The dual catheter assembly is then introduced into the patient using conventional procedures.

Once the dual catheter assembly is in the general vicinity of the stenosis or an especially tortuous site, only the first catheter typically is advanced further to take advantage of its generally smaller profile while the second catheter remains behind. Once at the stenosed site, balloon 18 of catheter 10 is inflated and deflated to partially open the occluded vessel. Optionally, catheter 10 includes a plurality of balloons which are preferably arranged in tandem, each balloon being successively larger in diameter than its distally neighboring balloon so that the doctor may have a variety of balloon sizes from which to choose from. In general, when the stenosis is sufficiently predilated to accommodate the larger sized catheter 50, the one or more balloons of first catheter 10 are advanced distally beyond the affected site so that shaft 12 may act as a guidewire for second catheter 50.

Second catheter 50 is then advanced to the site and the stent delivered by inflating either one of the concentric balloons 58 or 60 (or both in succession) depending on the circumstances. Optionally, second catheter 50 includes one or more additional balloons located more distally than concentric balloons 58 and 60 which may be used to further dilate the stenosis before stent delivery. Alternatively, second catheter 50 may include one or more additional balloons located more proximally than concentric balloons 58 and 60 which may be used for various post-dilation procedures. Each balloon on second catheter 50 may be independently inflated and deflated from entry port 84 of manifold 80. The dual catheter assembly, comprising first catheter 10 and second catheter 50, is removed from the patient when all the procedures are completed.

If pre-assembly is not desired, the catheters which comprise the dual catheter assembly may be put together in situ. For example, first catheter 10 is introduced into the occluded vessel to pre-dilate the stenosis. Once this completed, fitting 28 is removed and a guidewire extension is attached (if necessary) so that shaft 12 may be used as a stand alone guidewire for second catheter 50. At this point, second catheter 50 is threaded over shaft 12 starting from the proximal end of shaft 12 toward its distal end as catheter 50 is navigated to the stenosis. When properly situated, second catheter 50 is used in the same manner as previously described.

Although the dual catheter assembly and its method of use has been described with reference to particular embodiments, it should be understood that various features of the preferred embodiments may be used in any suitable combination. For example, a preferred device feature may be entirely eliminated such as coiled floppy tip 20 by replacing it with an extension of shaft 12. Similarly, even an especially preferred feature like a stent mounted on the second catheter may be entirely eliminated from the dual catheter assembly. In some situations, it may be desirable to mix the stated preferences between the first and second catheters. For example, a stent may be placed on a balloon on the first catheter instead of a second catheter. In another example, first catheter may be a multiple lumen balloon catheter having a manifold similar to that described for second catheter 50 instead of fitting 28. Accordingly, although the present invention has been described with reference to preferred embodiments, it should be appreciated that these embodiments are for purposes of illustration only and are not intended to limit the scope of the appended claims.

What is claimed is:

1. A dual catheter assembly comprising:
    a first catheter wherein the first catheter includes
        a shaft having a distal end and a proximal end;
        a first balloon mounted on the distal end of the shaft; and
        means for inflating the first balloon, and
    a second catheter slidably disposed on the first catheter wherein the second catheter can advance up to but not over the first balloon of the first catheter, the second catheter including
        an elongate tubular member having a distal end and a proximal end, the distal end being located proximal to the first balloon of the first catheter;
        a plurality of balloons mounted on the distal end of the elongate tubular member; and,
        means for inflating the plurality of balloons.

2. The dual catheter assembly as in claim 1 wherein the first catheter also functions as a guidewire.

3. The dual catheter assembly as in claim 2 wherein the first catheter has extension capability.

4. The dual catheter assembly as in claim 1 wherein the first catheter further includes a floppy tip.

5. The dual catheter assembly as in claim 4 wherein the floppy tip is preshaped.

6. The dual catheter assembly as in claim 4 wherein the floppy tip is shapeable before use.

7. The dual catheter assembly as in claim 1 wherein in the first catheter includes a plurality of balloons.

8. The dual catheter assembly as in claim 1 wherein the first catheter is a low profile balloon on a wire catheter.

9. The dual catheter assembly as in claim 1 wherein the first catheter further includes a removable fitting mounted on the proximal end of the shaft wherein the fitting includes a port for inflating and deflating the first balloon.

10. The dual catheter assembly as in claim 9 wherein the removable fitting also acts as a torquer.

11. The dual catheter assembly as in claim 1 wherein the first catheter further includes a non-removable fitting mounted on the proximal end of the shaft wherein the fitting includes a port for inflating and deflating the first balloon and wherein the fitting prevents the removal of the second catheter over the proximal end of the first catheter.

12. The dual catheter assembly as in claim 1 wherein the first catheter further includes a stent.

13. The dual catheter assembly as in claim 1 wherein the second catheter further includes a stent, the stent mounted onto one of the plurality of balloons.

14. The dual catheter assembly as in claim 13 wherein the second catheter has two balloons, a second balloon and a third balloon.

15. The dual catheter assembly as in claim 14 wherein the third balloon placed within the second balloon.

16. The dual catheter assembly as in claim 15 wherein the stent is carried by the second balloon.

17. The dual catheter assembly as in claim 14 wherein the second balloon and the third balloon are arranged in tandem.

18. The dual catheter assembly as in claim 14 wherein the third balloon has a larger inflation diameter than the second balloon.

19. The dual catheter assembly as in claim 1 wherein the second catheter is an over the wire catheter.

20. The dual catheter assembly as in claim 1 wherein the second catheter is a single operator exchange catheter.

21. The dual catheter assembly as in claim 1 wherein the second catheter further includes a separate lumen formed within the elongate tubular member for each balloon mounted thereon.

22. The dual catheter assembly as in claim 1 wherein the second catheter further includes a manifold mounted on to the proximal end of the elongate tubular member, the manifold comprising:
    a passageway for receiving the elongate tubular member;
    a conduit having an entry port; and
    a plurality of valves disposed within the conduit,
    wherein at least two of the valves have an opened position and a closed position, and include a first channel and second channel formed therein, the first channel in communication with the conduit to provide access through the valve when the valve is placed in the closed position, and the second channel in communication with the conduit to provide access through the valve as well as to fluidly couple the conduit to the passageway when the valve is placed in the opened position.

23. The dual catheter assembly as in claim 22 wherein the manifold valve includes a handle and an elongated stem and the elongated stem includes the first channel and the second channel.

24. The dual catheter assembly as in claim 23 wherein the first channel is substantially linear and the second channel is a T-shaped passageway.

25. A dual catheter assembly comprising:
    a first catheter wherein the first catheter includes
        a shaft having a distal end and a proximal end;
        a first balloon mounted on the distal end of the shaft; and
        means for inflating the first balloon, and
    a second catheter slidably disposed on the first catheter wherein the second catheter can advance up to but not over the first balloon of the first catheter, the second catheter including
        an elongate tubular member having a distal end and a proximal end, the distal end being located proximal to the first balloon of the first catheter;
        a second balloon mounted on the distal end of the elongate tubular member;
        a stent carried by the second balloon; and,
        means for inflating the second balloon.

26. The dual catheter assembly as in claim 25 wherein the first catheter also functions as a guidewire.

27. The dual catheter assembly as in claim 26 wherein the first catheter has extension capability.

28. The dual catheter assembly as in claim 25 wherein the second catheter includes one or more additional balloons.

29. The dual catheter assembly as in claim 28 wherein the second catheter has two balloons.

30. The dual catheter assembly as in claim 29 wherein the two balloons are in a concentric arrangement.

31. A dual catheter assembly
a first catheter wherein the first catheter includes
a shaft having a distal end and a proximal end;
a first balloon mounted on the distal end of the shaft;
a stent mounted onto the first balloon; and,
means for inflating the first balloon, and
a second catheter slidably disposed on the first catheter wherein the second catheter can advance up to but not over the first balloon of the first catheter, the second catheter including
an elongate tubular member having a distal end and a proximal end, the distal end being located proximal to the first balloon of the first catheter;
at least one balloon mounted on the distal end of the elongate tubular member; and,
means for inflating the at least one balloon.

32. A kit comprising:
a first catheter wherein the first catheter includes
a shaft having a distal end and a proximal end;
a first balloon mounted on the distal end of the shaft; and
means for inflating the first balloon, and
a second catheter capable of being slidably disposed on the first catheter such that the second catheter can advance up to but not over the first balloon of the first catheter, the second catheter including
an elongate tubular member having a distal end and a proximal end, the distal end being such that it remains located proximal to the first balloon of the first catheter when the second catheter is slidably disposed on the first catheter;
a plurality of balloons mounted on the distal end of the elongate tubular member; and,
means for inflating the plurality of balloons.

33. A kit comprising:
a first catheter wherein the first catheter includes
a shaft having a distal end and a proximal end;
a first balloon mounted on the distal end of the shaft; and
means for inflating the first balloon, and
a second catheter capable of being slidably disposed on the first catheter such that the second catheter can advance up to but not over the first balloon of the first catheter, the second catheter including
an elongate tubular member having a distal end and a proximal end, the distal end being such that it remains located proximal to the first balloon of the first catheter when the second catheter is slidably disposed on the first catheter;
a second balloon mounted on the distal end of the elongate tubular member;
a stent carried by the second balloon; and,
means for inflating the second balloon.

* * * * *